United States Patent [19]

Nowacki et al.

[11] Patent Number: 4,934,353

[45] Date of Patent: Jun. 19, 1990

[54] LITHOTRIPTER HAVING ROTATABLE VALVE FOR REMOVAL OF ELECTRODE STRUCTURE

[76] Inventors: Christopher Nowacki, 1552 Chickamauga, Long Grove, Ill. 60047; Mark T. Horbal, 2 South 530 Iroquois Court West, Warrenville, Ill. 60555

[21] Appl. No.: 415,613

[22] Filed: Oct. 2, 1989

[51] Int. Cl.[5] .............................................. A61B 17/22

[52] U.S. Cl. .................................. 128/24 A; 606/128; 313/119

[58] Field of Search ............. 128/24 A, 328; 606/127, 606/128; 313/119, 120, 122, 125

[56] References Cited

U.S. PATENT DOCUMENTS

| | | | |
|---|---|---|---|
| 989,905 | 4/1911 | Glasgow | 313/119 |
| 4,608,983 | 9/1986 | Müller et al. | 128/24 A |
| 4,630,607 | 12/1986 | Duinker et al. | 128/24 A |
| 4,730,614 | 3/1988 | Lacruche et al. | 606/128 |

*Primary Examiner*—Kyle L. Howell
*Assistant Examiner*—K. M. Pfaffle

[57] ABSTRACT

A lithotripter is provided with an upwardly opening reflector filled with water. A valve is secured to the undersurface of the member providing the reflector. A bore extends axially through the valve body in alignment with a bore in the reflector member to accommodate an electrode assembly. A disc is mounted in the body and also has a bore aligned with the first two mentioned bores to accommodate the electrode assembly. The electrode assembly can be partially withdrawn to clear the bore in the reflector member and also the bore in the disc, but blocking the passage of water through the valve body bore. The disc is then rotated to move the valve disc out of alignment with the reflector member body to prevent further loss of water from the reflector.

8 Claims, 2 Drawing Sheets

LITHOTRIPTER HAVING ROTATABLE VALVE FOR REMOVAL OF ELECTRODE STRUCTURE

BACKGROUND OF THE PRESENT INVENTION

Reduction of kidney stones and other concretions in the human body by a lithotripter is well known. A truncated ellipsoidal reflector is provided with a spark gap at the first focus point of the elliposoid. The second focus point of the ellipsoid is beyond the truncated end of the reflector, and the reflector is positioned so that the second focus point lies on the kidney stone or other concretion to be disintegrated. The reflector is filled with water, and the water in the reflector either directly engages the human body, or engages it through a flexible diaphragm of rubber or the like. An electrical spark across the gap at the first focus point causes flashing of a certain amount of water into steam, and in general generates a shockwave which is focused by the walls of the reflector and which passes through the water and through the tissues of the human body to the concretion which is to be disintegrated.

The spark gap is defined by a pair of electrodes which are disposed in spaced, aligned relation to one another. The voltage that causes the spark across the gap is on the order of 12K volts to 30K volts. This high voltage, coupled with frequent formation of sparks across the gap between the electrodes leads to erosion and deterioration of the electrodes. As a result, electrodes typically have to be replaced at least once during a treatment session for a patient, which treatment session may last on the order of one hour. Since the electrodes are under water, it has in the past been necessary to drain the reflector before the electrodes could be removed, and then to refill the reflector. This has caused various problems, the most obvious of which is the time delay during which the patient must lie on a treatment table, or in the case of certain lithotripters, must be left submerged in a water bath.

OBJECTS AND SUMMARY OF THE PRESENT INVENTION

It is an object of the present invention to provide a lithotripter with a valve through which the electrode structure is inserted, through which it can be withdrawn for replacement without draining of the water from the lithotripter reflector.

A further object of the present invention is to provide a valve in a lithotripter through which the electrode assembly is inserted and withdrawn in a step-wise fashion, wherein the valve includes a rotatable disc selectively to open or close a passageway for insertion and removal of the electrode structure.

In carrying out the foregoing and other objects and advantages of the present invention, an upwardly opening reflector is provided. The top end of the reflector, which is ellipsoidal, is truncated, and is provided with an overlying rubber or the like diaphragm. The reflector and the space beneath the diaphragm are filled with water. The reflector is upwardly opening, and is disposed about a substantially vertical axis. Electrode structure of the present invention extends into the bottom of the reflector along the axis of rotation. The electrode structure includes a cylindrical body of nonconducting material carrying a pair of electrodes extending upwardly beyond the upper end of the cylindrical body, and having lower ends extending radially outwardly from the body for making contact with fixed electrical contacts, and also for latching the electrode structure in place. An electrode valve structure is secured to the bottom of the structure which includes the electrode. The valve includes a fixed body, and a rotatable disc therein. The valve body and the valve disc are provided with holes radially spaced from the center of the valve. These holes can be aligned, where they can be moved out of alignment by rotation of the valve disc. When the holes are out of alignment, water cannot drain through the valve from the reflector. The electrode structure is inserted through the hole in the valve body, and this seals the valve so that water cannot drain from the reflector. The disc is then rotated to bring the hole in the disc into alignment with the hole in the valve body, and the electrode structure is inserted the rest of the way. Removal of the electrode structure is a reverse of the foregoing, and as a result electrodes can be removed and replaced without the necessity of draining water from the reflector.

THE DRAWINGS

The present invention will best be understood when the following specifications is read in connection with the accompanying drawings wherein.

DETAILED DESCRIPTION OF THE ILLUSTRATED EMBODIMENT

Figure 1:
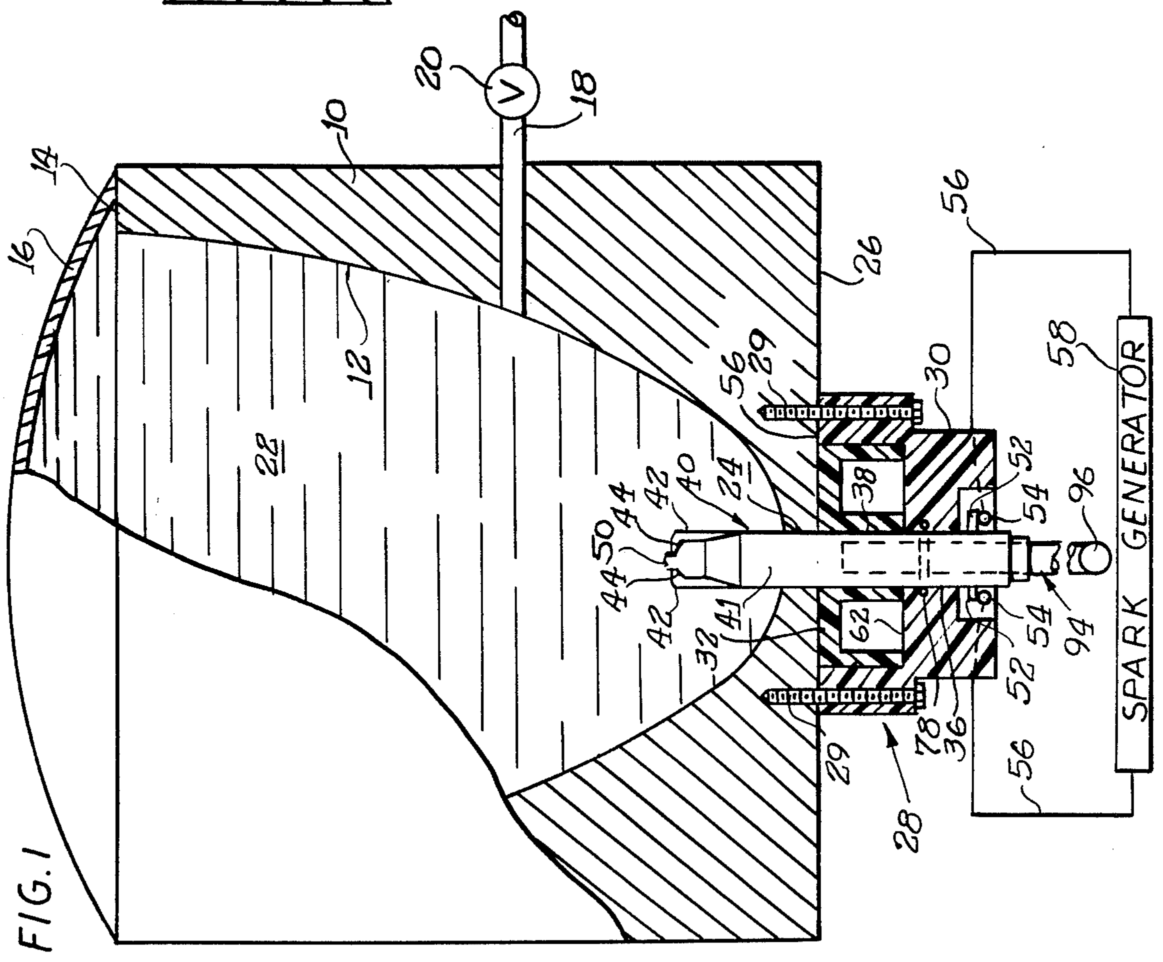
FIG. 1 is an axial section, partly in front view, of the reflector, electrode structure, and valve disc of a lithotripter constructed in accordance with the present invention.

Turning now in greater particularity to the drawings, and first to FIG. 1, there will be seen a lithotripter reflector member 10 having an internal reflective surface 12 forming a portion of an ellipsoid. The structure 10 and the reflector are truncated at 14, and a rubber or the like diaphragm 16 overlies the open upper end of the ellipsoidal reflector. A water supply pipe 18 extends radially into the cavity within the reflector 12 and is provided with a valve 20 for supplying water to and removing water from the reflector cavity. The reflector during use is filled with water, 22 which extends above the truncated top of the reflector and causes the diaphragm 16 to billow upwards in convex external shape as shown. The periphery of the diaphragm is secured to upper end of the structure 10 by any suitable or known means.

At the lower end of the reflector structure, and specifically at the apex of the reflector surface, there is provided a bore 24 extending from the reflector surface down to the outer, lower surface 26 of the structure 10. An electrode valve 28 constructed in accordance with the present invention is secured against the lower surface of the structure 10 by means such as bolts 29. The valve 28 includes a valve body 30 and a valve disc 32 which is rotatably mounted within the body. The body 30 is provided with a bore 36 which extends along the projected axis of rotation of the ellipsoidal reflector 12, and the disc 32 has a bore 38 which can be aligned with the bore 36 and with the bore 24 by rotation of the valve disc. The alignment position, the bores 36 and 38 being aligned with the bore 24, is illustrated in FIG. 1.

An electrode structure 40 extends through the bores. This electrode structure is shown and disclosed in greater detail in our copending application entitled, "ELECTRODE STRUCTURE FOR LIIHOTRIPTER", filed Sept. 11, 1989 under Ser. No. 405,425. For purposes of the present disclosure it is sufficient to state that the electrode structure includes a cylindrical body 41 carrying a pair of electrodes 42 which extend above the upper end of the cylindrical body and are curved in toward one another to provide confronting faces 44 defining a spark gap 50. The electrodes 42 extend nearly the entire length of the cylindrical body 41, which is preferably made of nylon or other suitable plastic resin material, and extend laterally therefrom at 52 to position movable electrical contacts to the fixed electrical contacts 54. The fixed electrical contacts are connected by means such as wires 56 to a spark generator 98.

Figure 4:
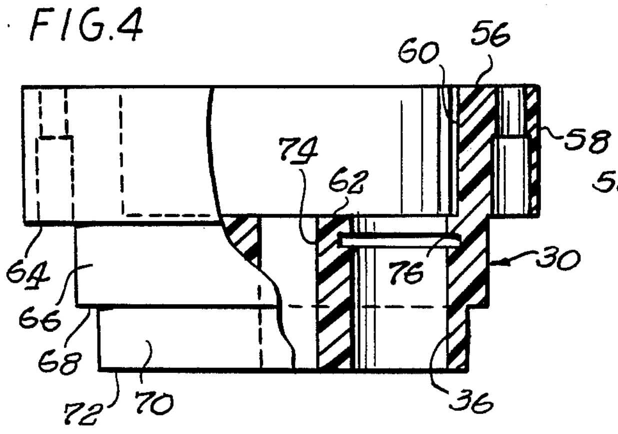
FIG. 4 is an axial sectional view through the valve body.
Figure 5:
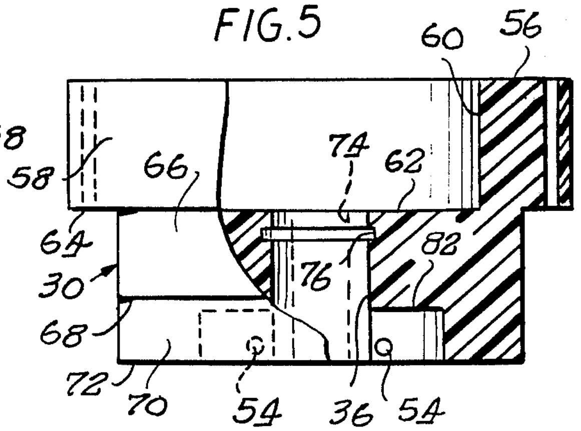
FIG. 5 is a view similar to FIG. 4 but taken at right angles thereto.
Figure 6:
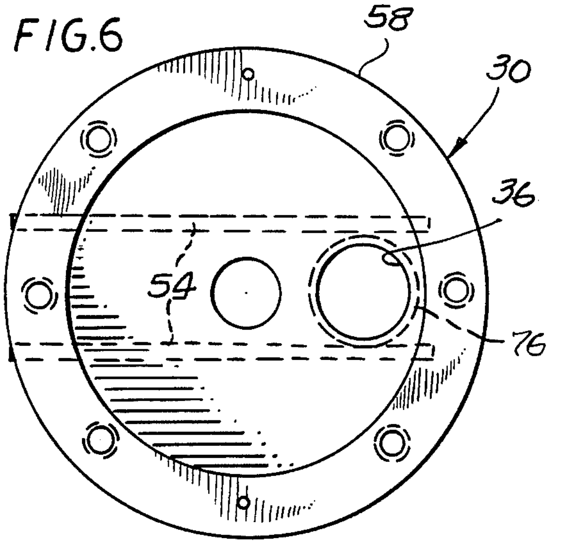
FIG. 6 is a top view of the valve body.

As will be understood the electrodes are made of electrically conductive material, and specific example which works satisfactorily is brass. The structure of the base 30 of the valve 28 will be seen particularly in FIGS. 4–6, as well as in FIGS. 1–3. The base includes an upper flat surface 56 and has an upper cylindrical section 58 with suitable axially extending bores therein for receipt of the various mounting bolts 29. The cylindrical portion 58 has a central cylindrical concavity 60 with a flat bottom surface 62. The surface 62 is substantially on a level with or slightly above the lower flat surface 64 of the upper cylindrical section 58.

A lower cylindrical section 66 of somewhat less diameter than the section 58 depends from and is integral with the section 58. Electrode structure 40 supported the fixed electrical contacts 54, which are cylindrical, as will be seen, and provide a lower surface or bottom 72 for the valve body.

The valve body is provided with a bore 74 of relatively small diameter and lying on the axis of the body. The bore opens upwardly into the cavity 60 and opens downwardly of the body. The bore 36 which is to receive the electrode assembly 40 also opens upwardly into the cavity 60 and downwardly of the body. Relatively adjacent the upper end of the bore 36 there is provided a circular recess 76 designed to accept an o-ring 78 to seal the body 41 of the electrode assembly 40 to the valve body 30 to prevent water leakage. The body 41 of the electrode assembly 40, and also the body 30 of the valve 28 are made of a suitable plastic resin material such as nylon. Accordingly, except for the o-ring 78 the electrode assembly can be moved axially through the bore 36 with relatively little resistance to movement.

Figure 8:
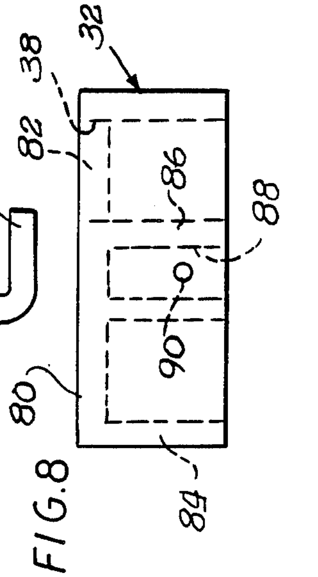
FIG. 8 is a side view of the valve disc.
Figure 7:
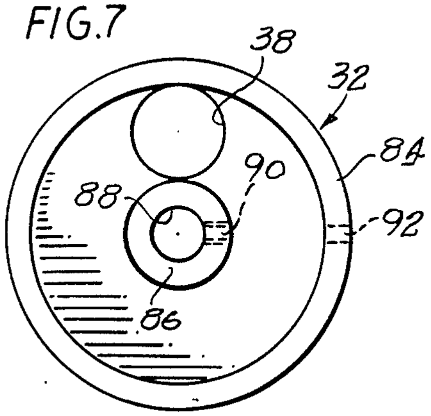
FIG. 7 is a bottom view of the valve disc.

The valve disc 32 is best seen in FIGS. 7 and 8, and the valve disc also is made of suitable plastic resin material such as nylon. Nylon is a preferred example, since it is dimensionally stable, it is strong, and it has excellent electrical resistance characteristics. The valve disc 32 includes an upper surface 80 beneath which there is a horizontal wall 82 which is circular. The diameter of the upper wall/bore 38 is such that it will fit within the concavity 60. A cylindrical skirt 84 depends from the horizontal wall 82 and is of the same outer diameter. The height of the skirt is such that the valve disc fits within the concavity 60 with the top surface 80 of the valve disc coplanar with the top surface 56 of the valve body. The valve disc is completed by a depending cylindrical boss 86 having its lower end coplanar with the lower edge of the skirt 84. The boss 86 is provided with a cylindrical bore 88 which is capped at the upper end by wall 82. A radial bore 90 extends through the side wall of the boss 86 for receipt of a set screw, and an aligned bore 92 is provided in the depending cylindrical wall 84 of the disc to permit screwdriver access to turn a set screw in the bore 90.

Figure 3:
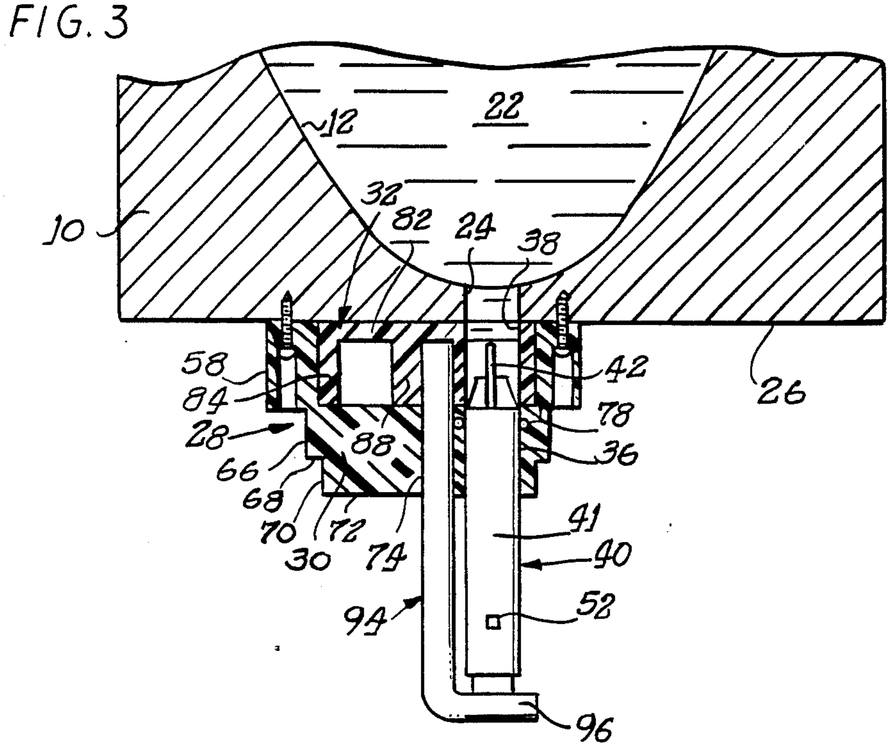
FIG. 3 is an axial sectional view similar to FIG. 2, showing the electrode structure in a position being withdrawn.

An L-shaped rod or handle 94 has a diameter substantially the same as the bore 74, but rotatable therein, and is also of substantially the same diameter as the bore 88 to form a relatively snug fit therein. A set screw threaded through the bore 90 clamps the rod in place. A lateral arm 96 on the handle 94 permits rotary turning of the disc 32, and also serves as a stop for the electrode assembly 40 as illustrated in FIG. 3 so that the electrode assembly can be axially withdrawn downwardly far enough to permit turning of the disc 32, while at the same time ensuring that the electrode assembly cannot be axially removed too far, and particularly not past the o-ring 78 so that water cannot escape from the reflector 12 through the bore 36. When electrode assembly has been withdrawn to the position shown in FIG. 3, the lateral arm 96 of the handle 94 blocks further withdrawal, and affords rotation by manual control of the valve disc, thereby shifting the bore 38 away from alignment with the bore 24, and sealing off the bottom end of the bore 24 with the top surface 80 of the valve disc 32. The electrode assembly then can be completely withdrawn.

Figure 2:
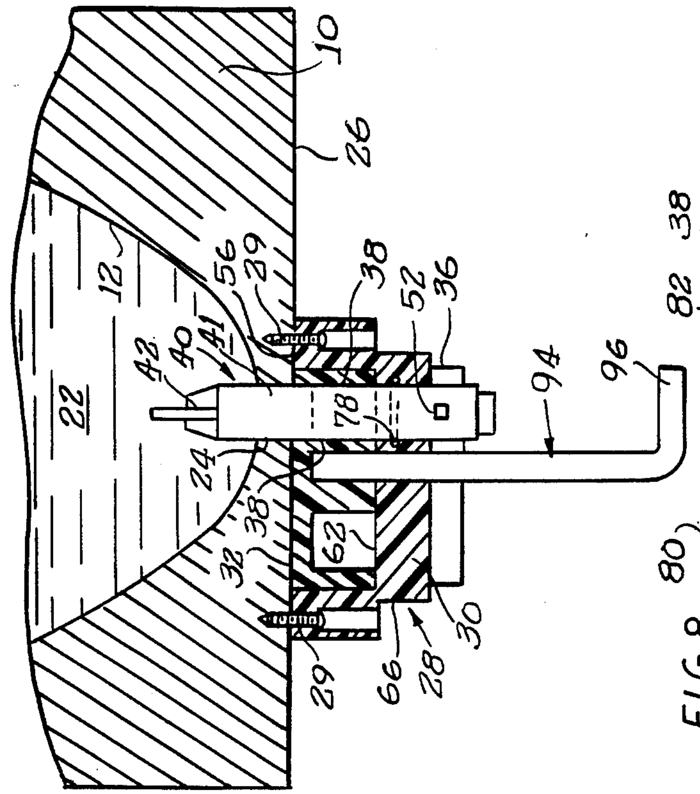
FIG. 2 is a fragmentary axial sectional view similar to a portion of FIG. 1, but taken at right angles thereto.

Insertion of a new electrode assembly is in the reverse. It is pushed up into the bore 36 until the electrodes 42 lightly touch the underside of the wall 82. The lateral projection 96 of the handle then is rotated to position it beneath the electrode assembly 40. This realigns the bore 38 with the bore 24, and the electrode assembly can be further pushed up into position as shown in FIG. 2. The electrode assembly then is rotated 90 degrees to position the movable contacts 52 on top of the fixed contacts 54 to complete the electrical connection from the wires 56 to the electrodes 42. It will be appreciated that there can be a reasonably tight fit of the movable and fixed contacts in that the fixed contacts are cylindrical, whereby the square movable contacts 52 can cam up over the fixed contacts, axially movement generally being somewhat resisted by the o-ring 78.

It will now be apparant that with the present lithotripter valve structure an electrode assembly can be quickly replaced without draining the water from the reflector 12. A very small amount of water will be lost, and the valve body therefore is provided with a drainhole (not shown) at an appropriate position for disposing of the very small amount of water lost during an electrode exchange.

The specific example of the invention as herein shown and described is for illustrative purposes. Various changes in structure will no doubt occur to those skilled in the art, and will be understood as forming a part of the present invention, insofar as they fall within the spirit and scope of the appended claims.

The invention is claimed as follows:

1. A lithotripter comprising means providing an upwardly opening reflector having an axis of revolution and a focus point and an apex on said axis, said reflector means having a substantially flat undersurface, said reflector means being adapted to be filled with a liquid such as water, a bore of predetermined diameter extending axially through said reflector means and upwardly opening through said apex into said reflector and downwardly opening through said undersurface, a valve including a valve body secured to said undersurface, said valve body including a cylindrical upwardly opening cavity disposed below said bore, said cavity having an axis of rotation offset relative to said bore and having a valve body bore of said predetermined diameter and aligned with said first mentioned bore and opening downwardly through said valve body, said valve including a valve disc rotatably disposed in said cavity and having a disc bore therethrough, said disc bore upon rotation of said valve disc being movable between a position aligned with and interconnecting said first mentioned bore and said valve body bore, and a non-aligned position with said valve disc blocking communication between said first mentioned bore and said valve body bore, an electrode assembly having an insulating cylindrical body of substantially said predetermined diameter and extendable through all of said bores in alignment, said electrode assembly having upper and lower ends and a pair of electrically conductive electrodes in spaced relation defining a spark gap disposed adjacent said upper end of said cylindrical body and disposed at said focus point, said electrode assembly being withdrawable from said first mentioned bore and said disc bore but blocking said valve body bore, rotation of said disc blocking said first mentioned bore to retain liquid in said reflector, said electrode assembly then being withdrawable from said valve body bore.

2. A lithotripter as set forth in claim 1 wherein said electrode assembly includes a pair of movable electrically conductive electrode contacts respectively connected to said electrodes and extending in diametrically opposite directions from said electrode body adjacent said lower end of said electrode body, a pair of fixed electrical contacts carried by said valve body, said movable electrode contacts respectively engaging upper portions of said fixed contacts and supporting said electrode assembly in said valve, said electrode assembly being rotatable to move said movable electrode contacts from said fixed contacts to permit withdrawal of said electrode assembly.

3. A lithotripter as set forth in claim 2 and further including an L-shaped handle extending axially from said disc and downwardly beyond said valve body to effect manual turning of said disc.

4. A lithotripter as set forth in claim 3 wherein said L-shaped handle has a lateral arm thereon alignable with said electrode assembly and of a proper length to limit withdrawal of said electrode assembly.

5. A lithotripter as set forth in claim 1 wherein said disc comprises an upper circular wall and a depending cylindrical peripheral skirt fitting in said concavity, said disc further having a depending central boss receiving a handle for rotating said disc, said skirt and said boss co-acting with said upper wall to provide clearance for turning said disc past said electrode assembly.

6. A lithotripter as set forth in claim 2 wherein said disc comprises an upper circular wall and a depending cylindrical peripherial skirt fitting in said concavity, said disc further having a depending central boss receiving a handle for rotating said disc, said skirt and said boss co-acting with said upper wall to provide clearance for turning said disc past said electrode assembly.

7. A lithotripter as set forth in claim 3 wherein said disc comprises an upper circular wall and a depending cylindrical peripherial skirt fitting in said concavity said disc further having a depending central boss receiving a handle for rotating said disc, said skirt and said boss co-acting with said upper wall to provide clearance for turning said disc past said electrode assembly.

8. A lithotripter as set forth in claim 4 wherein said disc comprises an upper circular wall and a depending cylindrical peripherial skirt fitting in said concavity, said disc further having a depending central boss receiving a handle for rotating said disc, said skirt and said boss co-acting with said upper wall to provide clearance for turning said disc past said electrode assembly.

* * * * *